United States Patent
Takahashi

(10) Patent No.: US 6,292,577 B1
(45) Date of Patent: *Sep. 18, 2001

(54) RESEMBLANCE RETRIEVAL APPARATUS, AND RECORDING MEDIUM FOR RECORDING RESEMBLANCE RETRIEVAL PROGRAM

(75) Inventor: Masanobu Takahashi, Tokyo (JP)

(73) Assignee: Mitsubishi Denki Kabsuhiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/070,739

(22) Filed: May 1, 1998

(30) Foreign Application Priority Data

May 27, 1997 (JP) .................................................. 9-136816

(51) Int. Cl.[7] ........................................................ G06K 9/46
(52) U.S. Cl. ........................ 382/128; 382/190; 382/305; 707/6
(58) Field of Search ................................... 382/128, 133, 382/190, 305; 707/1, 3, 6

(56) References Cited

U.S. PATENT DOCUMENTS

| | | | | |
|---|---|---|---|---|
| 4,672,683 | * | 6/1987 | Matsueda ............................ | 382/305 |
| 4,817,050 | * | 3/1989 | Komatsu et al. ..................... | 707/10 |
| 5,659,742 | * | 8/1997 | Beattie et al. ........................ | 707/3 |
| 5,878,746 | * | 3/1999 | Lemelson et al. ................... | 382/190 |
| 5,893,095 | * | 4/1999 | Jain et al. ........................... | 382/305 |
| 5,899,999 | * | 5/1999 | De Bouet ............................ | 707/104 |
| 5,923,779 | * | 7/1999 | Ohmi et al. .......................... | 382/190 |
| 5,970,164 | * | 10/1999 | Bamberger .......................... | 382/128 |
| 5,974,201 | * | 10/1999 | Chang et al. ........................ | 382/305 |
| 5,991,755 | * | 11/1999 | Noguchi et al. ..................... | 707/3 |
| 6,016,487 | * | 1/2000 | Rioux et al. ......................... | 707/3 |
| 6,115,717 | * | 9/2000 | Mehrotra et al. .................... | 382/190 |
| 6,173,275 | * | 1/2001 | Caid et al. ........................... | 382/190 |
| 6,175,828 | * | 1/2001 | Kuromusha et al. ................. | 707/3 |
| 6,181,818 | * | 1/2001 | Sato et al. ........................... | 382/305 |
| 6,182,069 | * | 1/2001 | Niblack et al. ...................... | 707/6 |

OTHER PUBLICATIONS

Hou et al. "Medical Image Retrieval by Spatial Features." IEEE Int. Conf. on Systems, Man and Cybernetics, vol. 2, pp. 1364–1369, Oct. 1992.*

Yazdani et al. A Framework for Feature–Based Indexing for Spatial Databases. Proceedings, Seventh International Working Conference on Scientific and Statistical Database Management, Sep. 1994, pp. 259–269.*

Steven Salzberg, "A Nearest Hyperrectangle Learning Method", Machine Learning, 6 pp. 251–276, 1991.

David W. Aha, "Incremental, Instance–Based Learning of Indepedent and Graded Concept Descriptions", Proceedings of the Sixth International Workshop on Machine Learning, pp. 387–391, 1987.

* cited by examiner

Primary Examiner—Jon Chang
(74) Attorney, Agent, or Firm—Leydig, Voit & Mayer, Ltd.

(57) ABSTRACT

A resemblance retrieve apparatus comprises a retrieve condition set producing unit, and resemblance vector data with respect to subject vector data is retrieved and displayed with using a weight vector optimized to a retrieve condition as to each of retrieve conditions produced in the retrieve condition set producing unit.

5 Claims, 10 Drawing Sheets

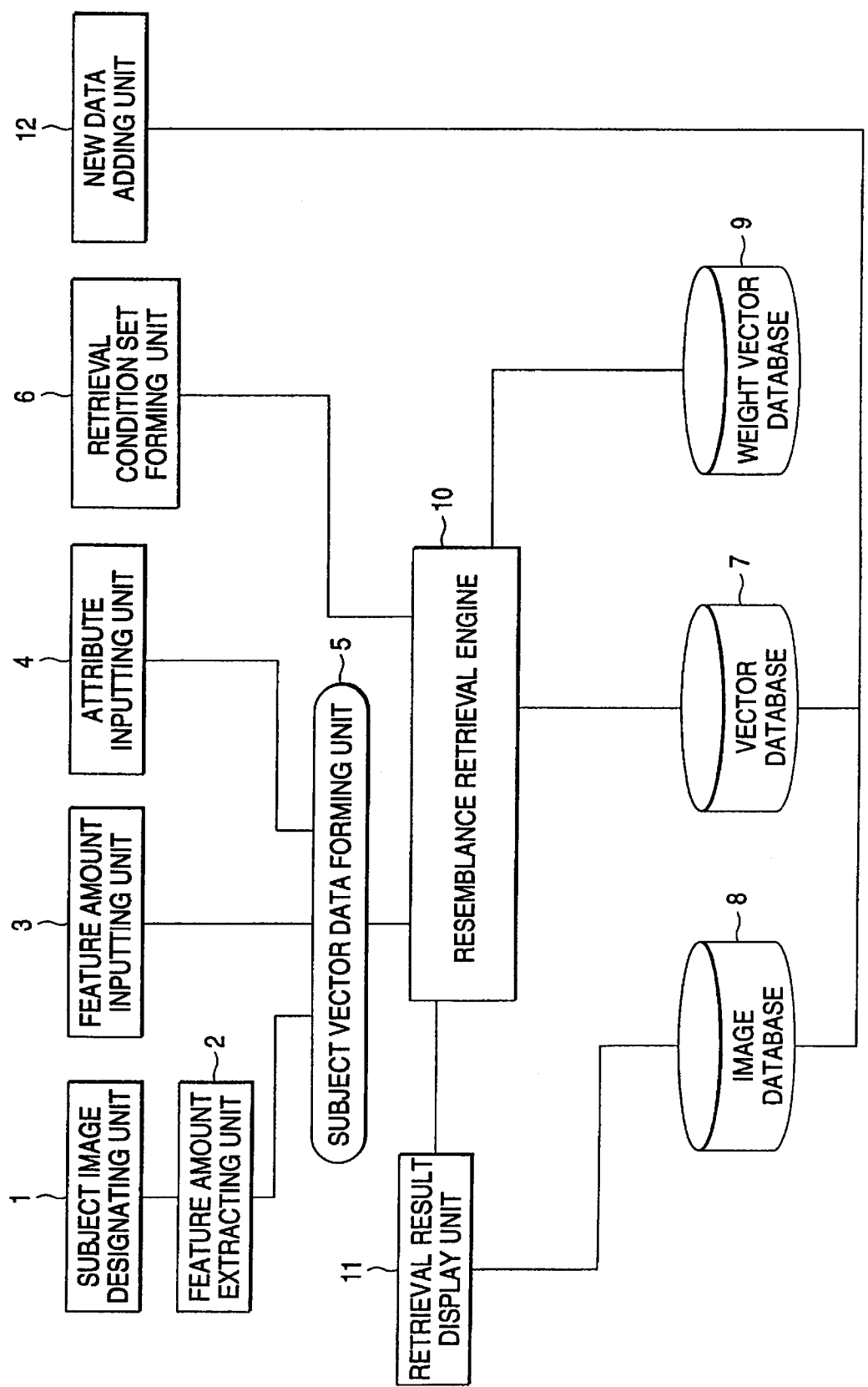

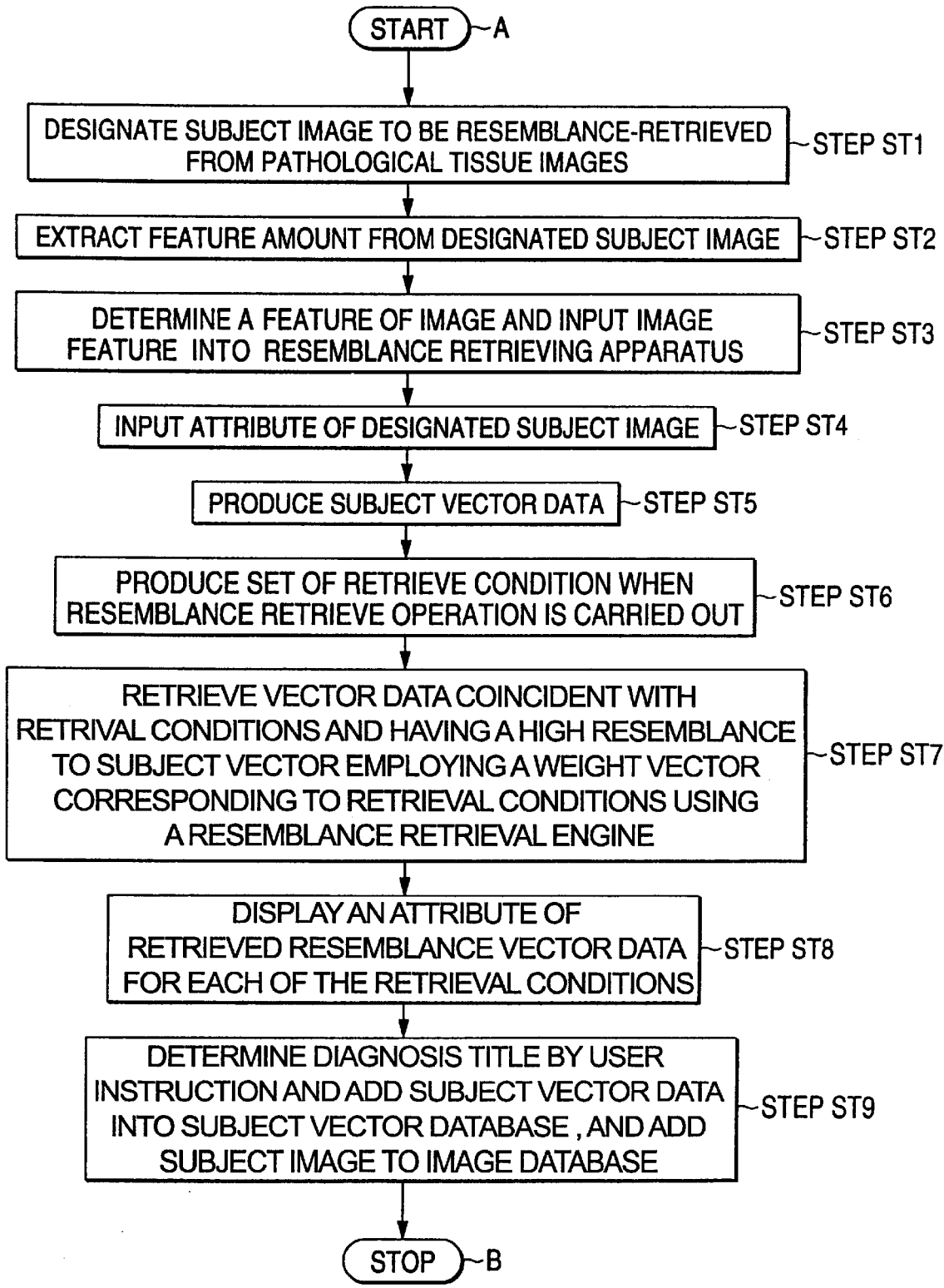

FIG. 3

| PATIENT NAME | PATIENT ID | IMAGE ID | DIMENSION OF TUMOR | AGE | DIAGNOSIS TITLE | AREA OF NUCLEAR REGION | AREA OF INTERSTITIAL REGION | DEGREE OF TEXTURE | EXISTANCE DEGREE OF FULFILL PATTERN |
|---|---|---|---|---|---|---|---|---|---|
| HANAKO MITSUBISHI | 970088 | 970123 | 2.5 | 35 | - | 0.12 | 0.74 | 0.2 | 0.05 |

FIG. 4

| NAME OF RETRIEVAL CONDITION | RETRIEVAL CONDITION |
|---|---|
| RETRIEVAL CONDITION 1 | DIAGNOSIS TITLE = TUMOR 1 |
| RETRIEVAL CONDITION 2 | DIAGNOSIS TITLE = TUMOR 2 |
| RETRIEVAL CONDITION 3 | DIAGNOSIS TITLE = TUMOR 3 |
| RETRIEVAL CONDITION 4 | DIAGNOSIS TITLE = TUMOR 4 OR 5 |
| RETRIEVAL CONDITION 5 | DIAGNOSIS TITLE = TUMOR 6 |
| RETRIEVAL CONDITION 6 | DIAGNOSIS TITLE = TUMOR 7 OR 8 |

FIG. 5

| | PATIENT NAME | PATIENT ID | IMAGE ID | DIMENSION OF TUMOR | AGE | DIAGNOSIS TITLE | AREA OF NUCLEAR REGION | AREA OF INTERSTITIAL REGION | DEGREE OF TEXTURE | EXISTANCE DEGREE OF FULFILL PATTERN |
|---|---|---|---|---|---|---|---|---|---|---|
| RETRIEVAL CONDITION 1 | 0.0 | 0.0 | 0.0 | 0.0 | 0.0 | 0.0 | 0.5 | 0.2 | 0.5 | 0.1 |
| RETRIEVAL CONDITION 2 | 0.0 | 0.0 | 0.0 | 0.0 | 0.0 | 0.0 | 0.3 | 0.3 | 0.0 | 0.0 |
| RETRIEVAL CONDITION 3 | 0.0 | 0.0 | 0.0 | 0.0 | 0.0 | 0.0 | 0.5 | 0.0 | 0.2 | 0.6 |
| RETRIEVAL CONDITION 4 | 0.0 | 0.0 | 0.0 | 0.0 | 0.0 | 0.0 | 0.7 | 0.7 | 0.0 | 1.0 |
| RETRIEVAL CONDITION 5 | 0.0 | 0.0 | 0.0 | 0.0 | 0.0 | 0.0 | 0.1 | 0.6 | 0.8 | 0.2 |
| RETRIEVAL CONDITION 6 | 0.0 | 0.0 | 0.0 | 0.0 | 0.0 | 0.0 | 0.0 | 0.9 | 0.0 | 0.5 |

FIG. 10
PRIOR ART

| PATIENT NAME | PATIENT ID | IMAGE ID | DIMENSION OF TUMOR | AGE | DIAGNOSIS TITLE | FEATURE AMOUNT | FEATURE AMOUNT | FEATURE AMOUNT | FEATURE AMOUNT |
|---|---|---|---|---|---|---|---|---|---|
| HANAKO MITSUBISHI | 970088 | 970123 | 2.5 | 35 | - | 0.05 | 0.12 | 0.74 | 0.2 |

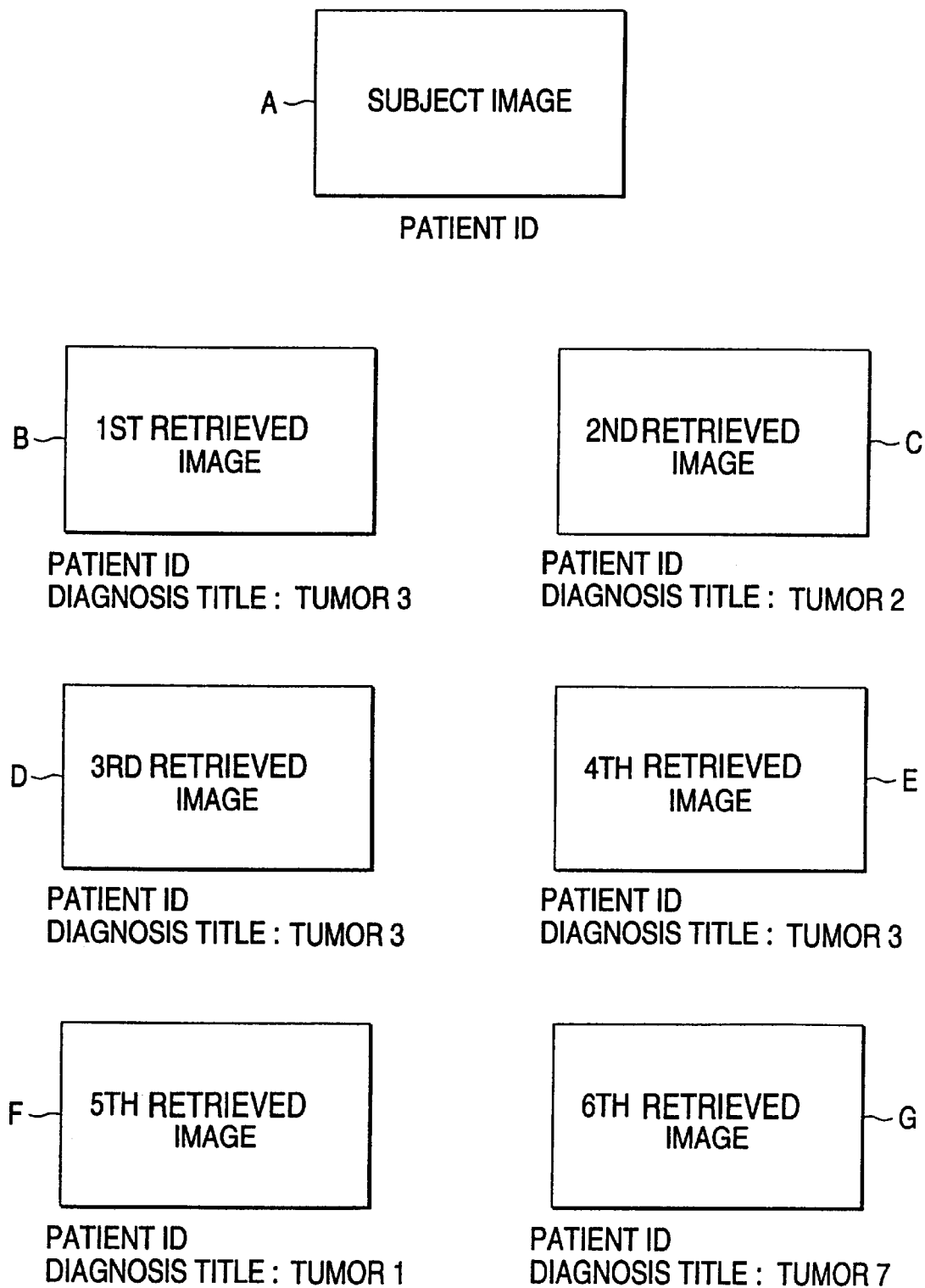

RESEMBLANCE RETRIEVAL APPARATUS, AND RECORDING MEDIUM FOR RECORDING RESEMBLANCE RETRIEVAL PROGRAM

BACKGROUND OF THE INVENTION

The present invention is related to a resemblance retrieval apparatus for retrieving stored subject data resembling subject data, with respect to a designated retrieval subject, from a saved data group, and also to a recording medium for recording such a resemblance retrieval program.

Conventional resemblance retrieval apparatus are described in, for instance, a publication "Incremental Instance-based Learning of Independent and Graded Concept Descriptions", D. Aha, Proceedings of the Sixth International Workshop on Machine Learning, 1987", and another publication "A Nearest Hyperrectangle Learning Method", S. Salzberg, Machine Learning, 6, pp. 251–276, 1991. FIG. 8 is a schematic block diagram showing an example of such a conventional resemblance retrieval apparatus.

In this drawing, reference numeral 1 is a subject image designating unit for designating an image of a retrieval subject; reference numeral 2 is a feature quantity extracting unit for extracting a feature quantity which quantitatively indicates the feature of the subject image designated by the subject image designating unit 1; reference numeral 4 shows an attribute input unit for inputting an attribute of the subject, other than the feature quantity related to the subject image; and reference numeral 5 represents a subject vector data forming unit for forming subject vector data in which both the feature quantity extracted by the feature quantity extracting unit 2 and the attribute input by the attribute input unit 4 are used as a vector structural elements. Reference numeral 7 denotes a vector database storing a plurality of vector data formed using the feature quantities and the attributes as vector elements; reference numeral 8 is an image database for storing a plurality of images corresponding to respective subjects; reference numeral 13 is a weight vector given to each of the vector elements of the vector data to calculate resemblance degree in a resemblance retrieval engine; and reference numeral 10 represents a resemblance retrieval engine for seeking vector data resembling subject vector data in the subject vector data forming unit 5 from a plurality of vector data stored in the vector database 7. Further, reference numeral 11 shows a retrieval result display unit for displaying the resemblance vector data retrieved by the resemblance retrieval engine 10, and also an image corresponding to this vector data; reference numeral 14 indicates an answer instructing unit for determining whether both the resemblance vector data designated by the resemblance retrieval engine 10 and the image are correct; reference numeral 15 shows a weight vector updating unit for updating the weight vector 13 based on the result determined by the answer instructing unit 14; and reference numeral 12 indicates a new data adding unit for newly entering vector data and images in the vector database 7 and the image database 8, respectively.

Now, operation will be explained. For instance, as to medical information, such as electronic medical diagnostic data and a medical image database, and as to design information, such as design drawings, that are stored, when data suitable for a new purpose are selected, the following resemblance retrieval technique for the vector data is applied. These data are rearranged as vector data stored in the database. Then, calculations are made to determine the resemblance degree between the vector data sought, which express a new purpose, and data saved in the database. The data in the database that most resembles the desirable vector data is found.

One example of such a purpose is aiding diagnoses of pathological tissue. In such a case, a pathological tissue image resembling a stored pathological tissue image is retrieved with respect to a pathological tissue image under examination. The purpose is to diagnose a disease by observing biological tissue. This pathological tissue diagnosis is mainly carried out to determine whether a tumor must be removed and to determine the sort of tumor.

FIG. 9 is a flow chart for describing the operation of the conventional resemblance retrieval apparatus. First, the subject image designating unit 1 designates a subject image for which a resemblance retrieval is to be performed, for, example, pathological tissue images to be examined (step ST1). Next, in the feature quantity extracting unit 2, a feature quantity for quantitatively expressing a feature of the designated subject image is extracted from the subject image (step ST2). Subsequently, in the attribute input unit 4, an attribute of the subject image designating unit 1 is input (step ST4). Examples of attributes of the subject image include patient name, patient ID, image ID, dimension of tumor, age of the patient, diagnosis title, and the like. It should be noted that since the diagnosis title is not yet determined at this stage, no diagnosis title is input. Subject vector data are produced using both the feature quantity extracted by the feature quantity extracting unit 2 and an attribute input into the attribute input unit 4 as vector elements (step ST101). FIG. 10 shows an example of subject vector data. Vector data having a high degree of resemblance to the subject vector data are retrieved from the vector database 7 by the resemblance retrieval engine 10, employing the weight vector 13 (step ST102).

In other words, assuming that the dimension (namely, the number of elements) of the vector data is selected to be "n", the subject vector data is $X=(x1, x2, \ldots, xn)$, and vector data stored in the vector database is $Y=(y1, y2, \ldots, yn)$. These data are used to calculate a degree of resemblance between the subject vector data and database vector data. The weight vector is $W=(w1, w2, \ldots, wn)$ and a resemblance degree $sim(X, Y)$ between the vector data X and the vector data Y is calculated based on the following formula:

[Formula 1]

$$sim(X, Y) = \sqrt{\sum_{i=1}^{n} \{wi \cdot \delta(xi, yi)\}^2}, \quad (1)$$

where $\delta(xi, yi)$ is equal to:

(xi−yi)/(section width of attribute "i"), when the attribute "i" has a continuous value;

0, when the attribute "i" has a discrete value, and xi=yi;

and 1, when the attribute "i" has a discrete value, and xi is not equal to yi. (2)

(It should be noted that the section width of the attribute "i" is equal to the absolute value of the difference between the maximum value of the attribute "i" and the minimum value thereof.)

In other words, the resemblance degree $sim(X, Y)$ is equal to the weighted distances X and Y, the symbols of which are inverted.

As previously described, when all of the vector data stored in the vector database 7 are set as Y, the degree of resemblance sim(X, Y) between these vector data and subject vector data is calculated. The maximum, or highest, degree of resemblance is selected to retrieve the vector data most closely resembling the subject vector data. When several vector data have the same maximum degree of resemblance, any one of these vector data may be selected. For instance, the first selected vector data may be employed or a selection from these vector data having the maximum degree of resemblance may be made at random.

In the retrieval result display unit 11, both a portion of the attributes of the retrieved resemblance vector data and an image corresponding to the resemblance vector data, among the images in the image database 8, are displayed (step ST103). FIG. 11 represents an example of a display screen in which six sets of resemblance images, including images, patient IDs, and diagnosis titles are displayed in the order of degree of resemblance. A user compares the subject image with the images displayed as a retrieval result. Then, the user determines which retrieved image truly resembles the subject image. There is a high possibility that the subject image is relevant to the diagnosis title corresponding to this resemblance image. As a result, display of the resemblance vector data and the resemblance image with respect to the subject image may give very important reference information, aiding a pathological tissue diagnosis.

Next, the user makes a decision concerning the diagnosis title with reference to the images displayed on the retrieval result display unit 11. If this diagnosis title is coincident with the diagnosis title of the resemblance vector data having the highest degree of resemblance, then the user chooses "CORRECT" in the answer instructing unit 14 because of this resemblance. Conversely, if this diagnosis title is not coincident with the resemblance vector data having the highest degree of resemblance, then the user chooses "INCORRECT" in the answer instructing unit 14 (step ST104).

Subsequently, the update vector 13 is updated in the weight vector updating unit 15 based upon the vector data selected as the most closely resembling vector by the resemble retrieval engine 10, the subject vector data, and the retrieval result designated by the user via the answer instructing unit 14 as to whether this retrieval result is "CORRECT" (step ST105).

Next, the subject vector data having the diagnosis title of the attribute of the subject image that is changed to the diagnosis title determined by the user is added to the vector database 7, and the subject image is added to the image database 8 by the new data adding unit 12 (step ST106).

Since the conventional resemblance retrieval apparatus is arranged as described, when this resemblance retrieval apparatus is utilized in pathological tissue diagnosis, there is a risk that an image with the correct diagnosis title may be dropped from the images displayed as potentially resembling images. For example, when the resemblance retrieval results shown as in FIG. 11 are displayed, resemblance images having the diagnosis titles of "tumor 1", "tumor 2", "tumor 3", and "tumor 7" are displayed. There is no problem when the subject image corresponds to one of these resemblance images with the diagnosis titles. However, if the correct diagnosis title of the subject image is the same as another diagnosis title which is not displayed, for example, resemblance images with diagnosis titles such as "tumor 4" and "tumor 5", there is a risk that the user may make a mistaken diagnosis because the user could not recognize the correct diagnosis title.

Also, there is another problem. Since only one sort of weight vector is used, even when the weight vector is optimized, it is practically difficult to greatly improve resemblance retrieval precision. For example, when this conventional resemblance retrieval apparatus is used in pathological tissue diagnosis, generally speaking, an optimum weight vector used when a resemblance image is retrieved from images with one diagnosis title, such as "tumor 1", is different from an optimum weight vector used when a resemblance image is retrieved from images of another diagnosis title, such as "tumor 2". This different weight occurs because the importance degree of the respective elements of the feature quantities are different from each other as to "tumor 1" and "tumor 2" when the degrees of resemblance are measured. The optimum weight vector used when the resemblance image is retrieved from combined images having different diagnosis titles, such as "tumor 1" and "tumor 2", will become an intermediate weight vector, between the optimum weight vector with respect to "tumor 1" and the optimum weight vector with regard to "tumor 2". As a result, for example, the resemblance retrieval precision when the resemblance image is retrieved from the images of "tumor 1" by employing the intermediate weight vector is reduced, as compared with the resemblance retrieval precision when the resemblance image is retrieved using the optimum weight vector with respect to "tumor 1". As described above, when resemblance image retrieval employing one sort of weight vector for all of the images containing all of the diagnosis titles, there is a problem in achieving the same effect as when the weight vector is optimized.

Also, when the only feature quantity extracted from the image as the feature quantity of the image is a portion of the subject vector data, it is not possible to use a feature quantity which can hardly be extracted. Furthermore, a feature of an image which is intentionally determined by the user cannot be utilized in the resemblance image retrieval operation.

SUMMARY OF THE INVENTION

The present invention has been made to solve the above-explained problem and, therefore, has an object to provide a resemblance retrieval apparatus with improved resemblance retrieval precision and having a low possibility that important resemblance data is absent from a retrieval result and also to provide a recording medium for recording a resemblance retrieval program.

A resemblance retrieval apparatus, according to a first aspect of the present invention, comprises a vector database storing vector data for a plurality of subjects and in which attributes characterizing the subjects are vector elements; a subject vector data forming unit for forming vector data for a designated resemblance retrieval subject; a retrieval condition set forming unit for forming retrieval conditions; a resemblance retrieval engine for retrieving vector data which satisfy the retrieval conditions and resemble the subject data, from vector data stored in the vector database, for each of the retrieval conditions; and a retrieval result display unit for displaying the vector data retrieved by the resemblance retrieval engine for each of the retrieval conditions.

A resemblance retrieval apparatus, according to a second aspect of the present invention, comprises an image database storing subject images corresponding to subjects; a vector database storing vector data for each of the subjects in which both a feature quantity quantitatively indicating a feature of the subject image and an attribute characterizing the subject are set as vector elements; a subject vector data forming unit for forming vector data based upon an image and an attribute of a designated resemblance retrieval subject; a retrieval condition set forming unit for forming retrieval conditions;

a resemblance retrieval engine for retrieving vector data satisfying the retrieval conditions and resembling the subject data, from the vector data stored in the vector database, for each of the retrieval conditions; and a retrieval result display unit for displaying the vector data retrieved by the resemblance retrieval engine for each of the retrieval conditions, in combination with the corresponding images.

A resemblance retrieval apparatus, according to a third aspect of the present invention, further comprises at least one of a feature quantity extracting unit for extracting a feature quantity of an image, and a feature quantity input unit for inputting a feature quantity of an image and employing as a feature quantity quantitatively indicating a feature of an image, at least one of a feature quantity extracted by the feature quantity extracting unit and a feature quantity input from the feature quantity input unit.

In a resemblance retrieval apparatus, according to a fourth aspect of the present invention, an image of biological tissue is used and, as a retrieval condition, a diagnosis title for pathological tissue diagnosis is employed.

In a resemblance retrieval apparatus, according to a fifth aspect of the present invention, as the feature quantity of the image, at least one of quantity of a nuclear region; area of the nuclear region; shape of the nuclear region; circular degree of the nuclear region; color of the nuclear region; chromaticity of the nuclear region; quantity of air space region; area of the air space region; shape of the air space region; circular degree of the air space region; quantity of an interstitial region; area of the interstitial region; shape of the interstitial region; circular degree of the interstitial region; color of the interstitial region; chromaticity of the interstitial region; quantity of a tubular region; area of the tubular region; shape of the tubular region; circular degree of the tubular region; texture of an image; a wavelet transformation value; degree to which an epithelium cell represents a two-layer structure in combination with a muscular epithelium cell; degree of texture; existence/absence of a nipple pattern; existence/absence of a mesh-shaped pattern; existence/absence of a necrotic substance; existence/absence of a fulfill pattern; color of an image; and chromaticity of the image.

A resemblance retrieval apparatus, according to a sixth aspect of the present invention, further comprises a weight vector database storing weight vectors corresponding to each of the retrieval conditions. The weight vectors employed by the resemblance retrieval engine are specified with respect to respective retrieval conditions.

A recording medium, according to a first aspect of the present invention, has recorded in the medium a resemblance retrieval program for forming vector data in which attributes characterizing resemblance retrieval subjects are set as vector elements; retrieving vector data resembling the subject vector data and satisfying the retrieval conditions from vector data for subjects stored in a vector database as to the retrieval conditions; and outputting retrieved results for each of the retrieval conditions.

A recording medium, according to a second aspect of the present invention, has recorded in it a resemblance retrieval program used to cause a computer to form vector data based on an image of a resemblance retrieval subject and an attribute characterizing the subject, in which a feature quantity quantitatively indicating a feature of a subject image and the attribute of the subject are vector elements; retrieve vector data resembling the subject vector data and also satisfying the retrieval conditions from vector data for subjects stored in a vector database for retrieval conditions; and output the retrieved results for each of the retrieval conditions, in combination with corresponding images.

BRIEF DESCRIPTION OF THE DRAWINGS

FIG. 1 is a block diagram for showing a resemblance retrieval apparatus according to a first embodiment of the present invention.

FIG. 2 is a flow chart indicating operations of the resemblance retrieval apparatus according to a first embodiment of the present invention.

FIG. 3 shows an example of subject vector data according to a first embodiment of the present invention.

FIG. 4 represents an example of a retrieval condition set according to a first embodiment of the present invention.

FIG. 5 shows an example of a weight vector according to a first embodiment of the present invention.

FIG. 10 shows an example of the subject vector data employed in the conventional resemblance retrieval apparatus.

FIG. 11 represents an example of the display image indicated in the conventional resemblance retrieval apparatus.

DETAILED DESCRIPTION OF THE PREFERRED EMBODIMENTS

First Embodiment

Figure 6:
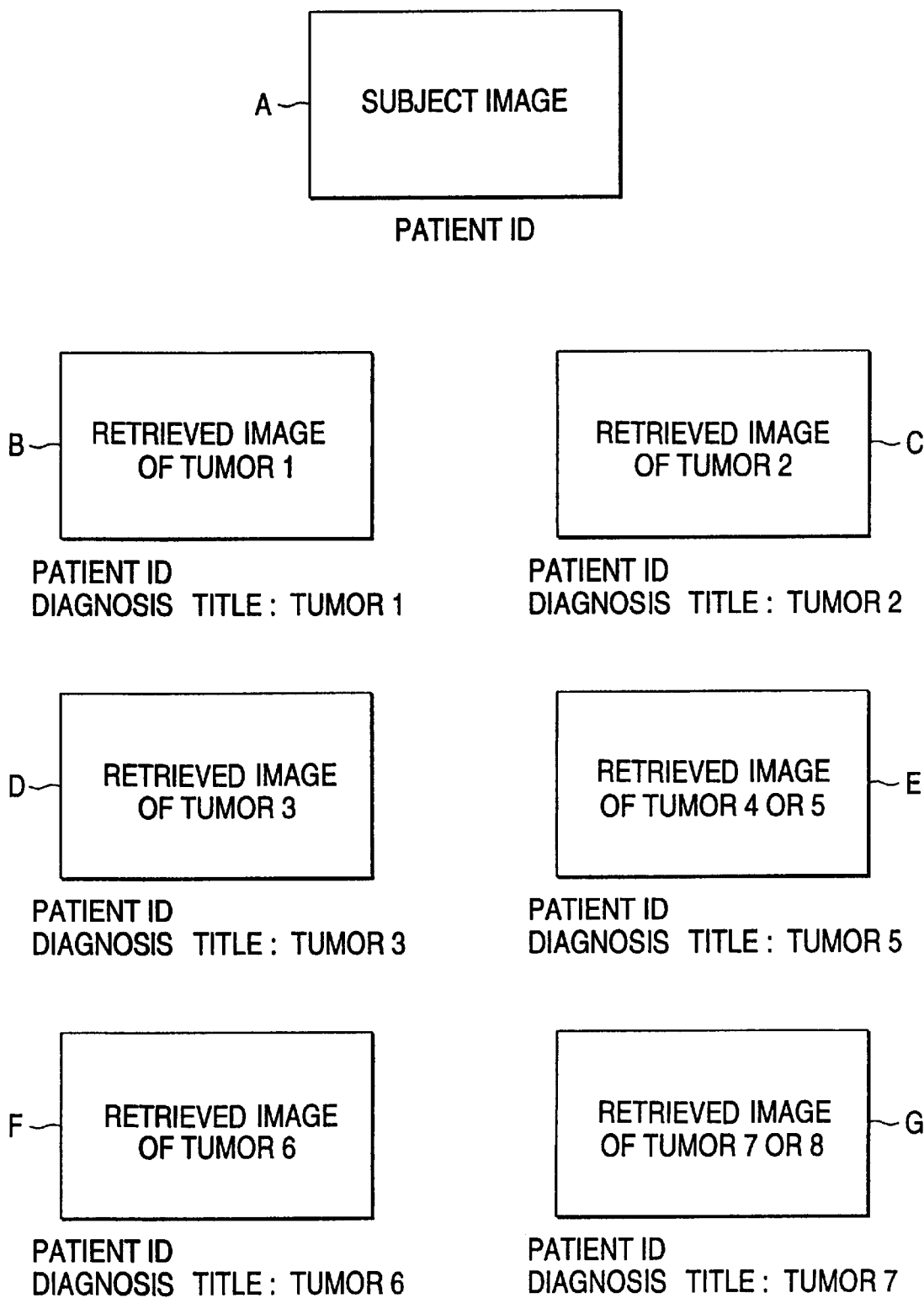
FIG. 6 represents an example of a display image indicated in the resemblance retrieval apparatus according to a first embodiment of the present invention.

FIG. 1 is a schematic block diagram of a resemblance retrieval apparatus according to the first embodiment of the present invention. In this drawing, reference numeral 1 shows a subject image designating unit for designating an image of a retrieval subject; reference numeral 2 denotes a feature quantity extracting unit for extracting a feature quantity which quantitatively indicates the feature of the subject image designated by the subject image designating unit 1; reference numeral 3 is an attribute input unit for inputting a feature quantity recognized by a user with respect to a subject image; reference numeral 4 shows an attribute input unit for inputting an attribute of a subject image, other than the feature quantity related to the subject image; and reference numeral 5 represents a subject vector data forming unit for forming subject vector data in which both the feature quantity extracted by the feature quantity extracting unit 2, the feature quantity input by the feature quantity input unit 3, and the attribute input by the attribute input unit 4 are used as vector elements. Reference numeral 6 shows a retrieval condition set producing unit; reference numeral 7 denotes a vector database for storing as a database a plurality of vector data for a plurality of subjects based on the vector data using the feature quantities, and the attributes as the vector elements; reference numeral 8 is an image database for storing a plurality of images corresponding to the plural subjects; reference numeral 9 is a weight vector database for storing a weight vector employed when a calculation is made of a degree of resemblance between vector data, in a resemblance retrieval operation, the weight vector database 9 storing a plurality of optimized weight vectors corresponding to respective retrieval conditions; and reference numeral 10 represents a resemblance retrieval engine for retrieving vector data resembling the subject vector data from a plurality of vector data stored in the vector database 7. The retrieval engine selects from the vector database 7 vector data having the attribute designated by the retrieval condition set producing unit 6, based on the weight vectors stored in the weight vector database 9. Further, reference numeral 11 shows a retrieval result display unit for displaying the vector data retrieved by the resemblance retrieval engine 10, and also an image corresponding to this vector data with respect to each of the retrieval conditions designated by the retrieval condition set producing unit 6. Reference numeral 12 indicates a new data adding unit for newly registering vector data and an image in the vector database 7 and the image database 8, respectively.

Operations of the resemblance retrieval apparatus according to the first embodiment of the present invention is now described. As in the conventional resemblance retrieval apparatus, the resemblance retrieval apparatus according to the invention retrieves a past pathological tissue image resembling a pathological tissue image under examination.

FIG. 2 is a flow chart for describing the operation of the resemblance retrieval apparatus according to the first embodiment of the present invention. First, the subject image designating unit 1 designates a subject image for which a resemblance retrieval is to be performed from pathological tissue images to be examined (step ST1).

Next, in the feature quantity extracting unit 2, a feature quantity, quantitatively expressing a feature of the designated subject image, is extracted from this subject image (step ST2). As examples of a feature quantity, for example, there are: the number of nuclear regions contained in an image; area of the nuclear region; number of interstitial regions contained in an image; and area of the interstitial regions. In this example, the area of a nuclear region and the area of an interstitial region are extracted. It should be noted that these feature quantities may be calculated using a computer. As an example, a method for determining the number of nuclear regions will now be explained.

(1). A neural network is used to determine whether an image in question is equal to a nucleus.
(2). In this neural network, an image produced by extracting only nuclei from an original image is formed.
(3). A labeling operation is carried out. In other words, the same label number is given to coupled nuclear regions.
(4). The quantity of labels is counted. In this example, the neural network used to determine whether the image in question corresponds to the nucleus defined in (1) employs a learning method; that is, an image in which a nuclear region has been previously recognized is employed. Color information such as R, G, B color data with respect to each of the pixels of an image is input. Then, while using as a teaching signal information indicating whether a pixel corresponds to a nucleus, a learning method is employed. If the image is not of a nucleus, then the output from the neural network is 1, whereas if the image is of a nucleus, then the output from the neural network is 0.

Thereafter, in the feature quantity input unit 3, the user of the resemblance retrieval apparatus makes his own judgment about a feature of the image and inputs this image feature (step ST3). As the feature quantity determined by this user, there are, for instance, degrees of texture and degrees of fulfill patterns.

Subsequently, in the attribute input unit 4, an attribute of the subject image designating unit 1 is input (step ST4). As attributes of the subject image, there are, for example, patient name, patient ID, image ID, dimension of a tumor, patient age, diagnosis title, and the like. It should be noted that since the diagnosis title for the subject image is not yet determined at this stage, no diagnosis title is input.

Next, subject vector data are prepared using the feature quantity extracted by the feature quantity extracting unit 2, the feature quantity input by the feature quantity input unit 3, and the attribute input to the attribute input unit 4 as vector elements (step ST5). In FIG. 3, there is shown an example of the subject vector data so prepared.

Next, in the retrieval condition set producing unit 6, a set of retrieval conditions used when a resemblance retrieval operation is carried out is produced (step ST6). FIG. 4 represents an example of a set of retrieval conditions when a diagnosis title is used as a retrieval condition.

As to the respective retrieval conditions of the retrieval condition set, vector data which is coincident with the retrieval condition set and also has a high degree of resemblance to the subject vector data is retrieved by the resemblance retrieval engine 10 from the vector database 7, employing a weight vector corresponding to the retrieval condition, from the weight vectors in the weight vector database 9 (step ST7).

The weight vector uses an optimum weight previously entered in the weight vector database 9 with respect to each of the retrieval conditions. FIG. 5 represents an example of the weight vectors employed for the respective retrieval conditions of the retrieval condition set of FIG. 4. In the retrieval condition set shown in FIG. 4, when a user wants to retrieve a resemblance image from all of images which may satisfy diagnosis titles corresponding to one of the retrieval conditions, as indicated in FIG. 5, weights related to attributes, such as patient name and the dimension of the tumor, are set to 0. The weight vectors may be optimized. For example, the weight updating method used in the conventional resemblance retrieval apparatus may be utilized, employing the vector data in the vector database. Alternatively, the user may determine mutual resemblance characteristics of the images in the image database, and the resemblance retrieval result may be quantitatively and automatically evaluated using the mutual resemblance characteristics as an evaluation value. Then, the resemblance retrieval result is evaluated using the vector data in the vector database, and the weight is automatically updated along a direction so that this evaluation result becomes better.

The resemblance retrieval operation is carried out as follows. Assuming that the dimension (namely, the number of structural elements) of the vector data is selected to be "n"; the subject vector data is $X=(x1, x2, \ldots, xn)$; vector data $Y=(y1, y2, \ldots, yn)$ is stored in the vector database and used to calculate the degree of resemblance with respect to the subject vector data; and weight is $W=(w1, w2, \ldots, wn)$, the degree of resemblance, $sim(X, Y)$, between the vector data X and the vector data Y may be calculated based on the formulae (1) and (2) in a calculation similar to the prior art. When all of the vector data satisfying the retrieval condition from the vector data stored in the vector database 7 are Y, the degree of resemblance $sim(X, Y)$ between these vector data and the subject vector data is calculated. The maximum, or highest, degree of resemblance is selected to retrieve the most similar vector data from the database 7. When more than one of the vector data has the same maximum degree of resemblance, any one of them may be selected. For instance, the first selected vector data may be employed or one of he vector data having the maximum resemblance degree may be selected at random.

Next, in the retrieval result display unit 11, both a portion of the attributes of the retrieved resemblance vector data and an image corresponding to the resemblance vector data, from the images saved in the image database 8, are displayed for every retrieval condition (step ST8). FIG. 6 represents an example of a display screen when images, patient IDs, and diagnosis titles are displayed.

The user determines the diagnosis title with reference to the content of the display screen, and then adds the subject vector data, into which a portion of the diagnosis title corresponding to the attribute of the subject image has been added, to the vector database 7 and also adds the subject image in the image database 8 using the new data adding unit 12 (step ST9).

The resemblance retrieval calculation of the subject image is realized using a resemblance retrieval program, and this resemblance retrieval program is recorded in a recording medium.

Although the feature quantity extracted by the feature quantity extracting unit 2 is directly used as a portion of the subject vector data in the first embodiment, this extracted feature quantity may be corrected by the user.

In the first embodiment, both the feature quantity extracted by the feature quantity extracting unit 2 and the feature quantity input from the feature quantity input unit 3 are used as the feature quantity of the image. Alternatively, only one of these feature quantities may be employed.

In accordance with the first embodiment, examples of feature quantities of the image include the area of nuclear regions, the area of interstitial regions, the degree of texturing, and the degree of the fulfill pattern. The feature quantity is not limited to these feature quantities. The following feature quantities, calculated using quantity of nuclear region, may be employed: area of nuclear region, shape of nuclear region, circular degree of nuclear region, color of nuclear region, chromaticity of nuclear region, quantity of air space region, area of air space region, shape of air space region, circular degree of air space region, quantity of interstitial region, area of interstitial region, shape of interstitial region, circular degree of interstitial region, color of interstitial region, chromaticity of interstitial region, quantity of tubular region, area of tubular region, shape of tubular region, circular degree of tubular region, texture of image, wavelet transformation value; degree to which an epithelium cell represents a two-layer structure in combination with a muscular epithelium cell; degree of texture; existence/absence of nipple pattern; existence/absence of mesh-shaped pattern; existence/absence of necrotic substance; existence/absence of fulfill pattern; color of image; and chromaticity of image. Alternatively, the feature quantity may be freely chosen by the user.

In the first embodiment, attributes of the image in the vector data may include patient name, patient ID, image ID, dimension of the tumor, patient age, and diagnosis title. Alternatively, other attributes may be employed. These attributes may be freely chosen by the user.

In the first embodiment, the retrieval condition is established in the retrieval condition set forming unit 6. Alternatively, frequently used retrieval conditions may be previously prepared and designated.

In the first embodiment, the diagnosis title is used as a retrieval condition. Alternatively, other attributes and other feature quantities may be employed as retrieval conditions.

In the first embodiment, weight vectors which have been optimized with respect to respective retrieval conditions are stored in the weight vector database 9. Alternatively, the weight vectors may be updated, based on the judgment of the user as to whether the resemblance retrieval result is correct, in a manner similar to the conventional resemblance retrieval apparatus. When there is no weight vector corresponding to a certain retrieval condition, this weight vector may be replaced by a weight vector corresponding to a retrieval condition approximating the certain retrieval condition. Alternatively, another weight vector may be newly produced based on a weight vector corresponding to a retrieval condition approximating the certain retrieval condition. Otherwise, when there is no weight vector corresponding to the retrieval condition, weight vectors are previously determined.

In accordance with the first embodiment, one of the resemblance vector data is retrieved with respect to each of the retrieval conditions, and then is displayed in connection with the image. Alternatively, a plurality of resemblance vector data may be retrieved, in the order of the degree of resemblance with respect to the respective retrieval conditions, and may be displayed in combination with the corresponding images.

Although the degree of resemblance is calculated using the formulae (1) and (2) in the first embodiment, the present invention is not limited thereto, but may employ other calculating methods.

The first embodiment includes one example of a pathological tissue image under examination, and a pathological tissue image resembling a previously recorded pathological tissue image is retrieved. A similar effect may be achieved in resemblance retrieval operations related to an image for cell diagnosis, an X-ray image, and any other medical image, classifications of agricultural products, and other resemblance retrieval operations of various images.

Images are not necessarily utilized to perform the resemblance retrieval operation. For instance, a similar effect may be achieved in retrieving disease samples in medical diagnostic data, namely, generally speaking, in retrieving resemblance vector data.

Second Embodiment

Figure 7:
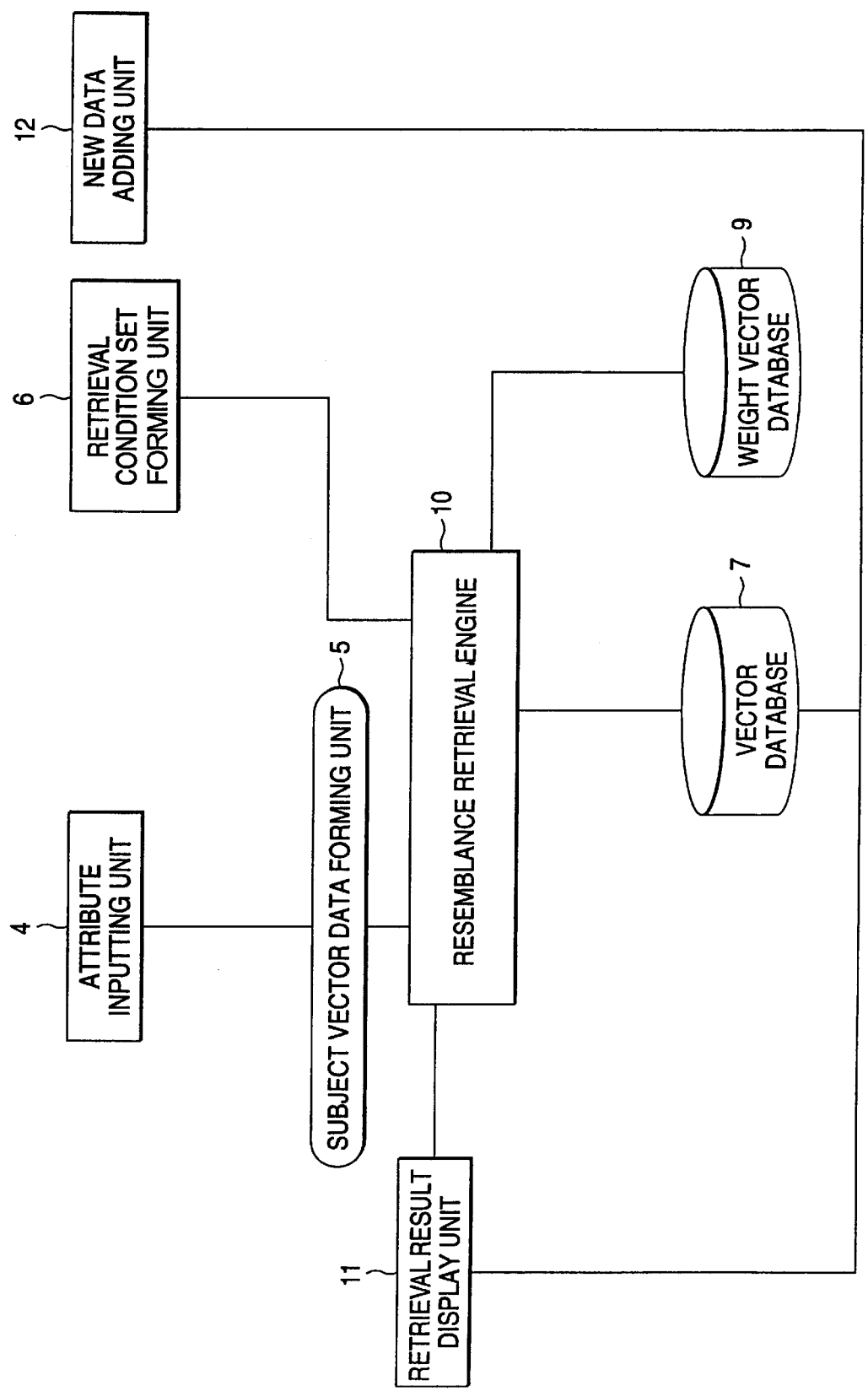
FIG. 7 is a block diagram showing a resemblance retrieval apparatus according to a second embodiment of the present invention.
Figure 8:
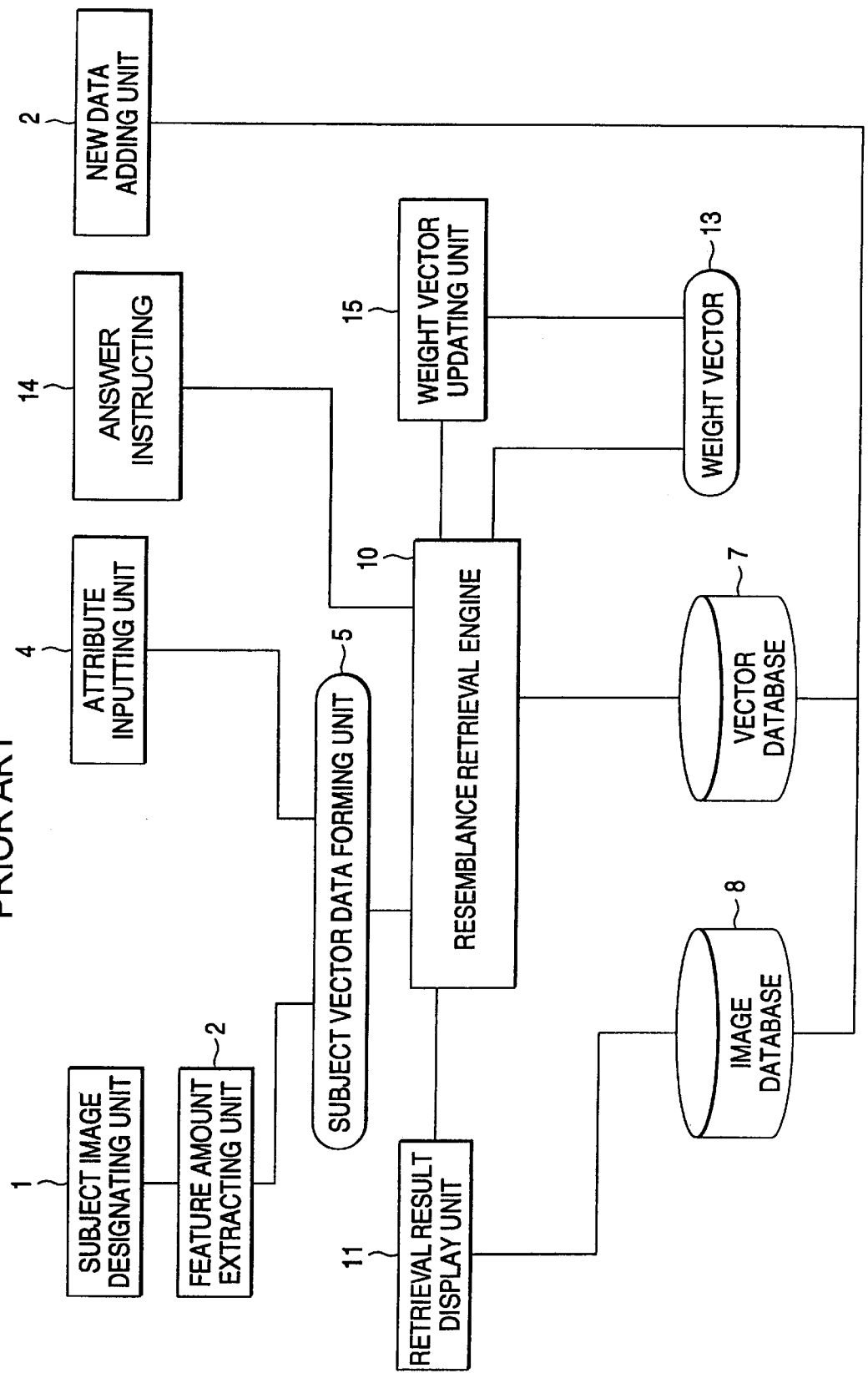
FIG. 8 is a block diagram representing the conventional resemblance retrieval apparatus.
Figure 9:
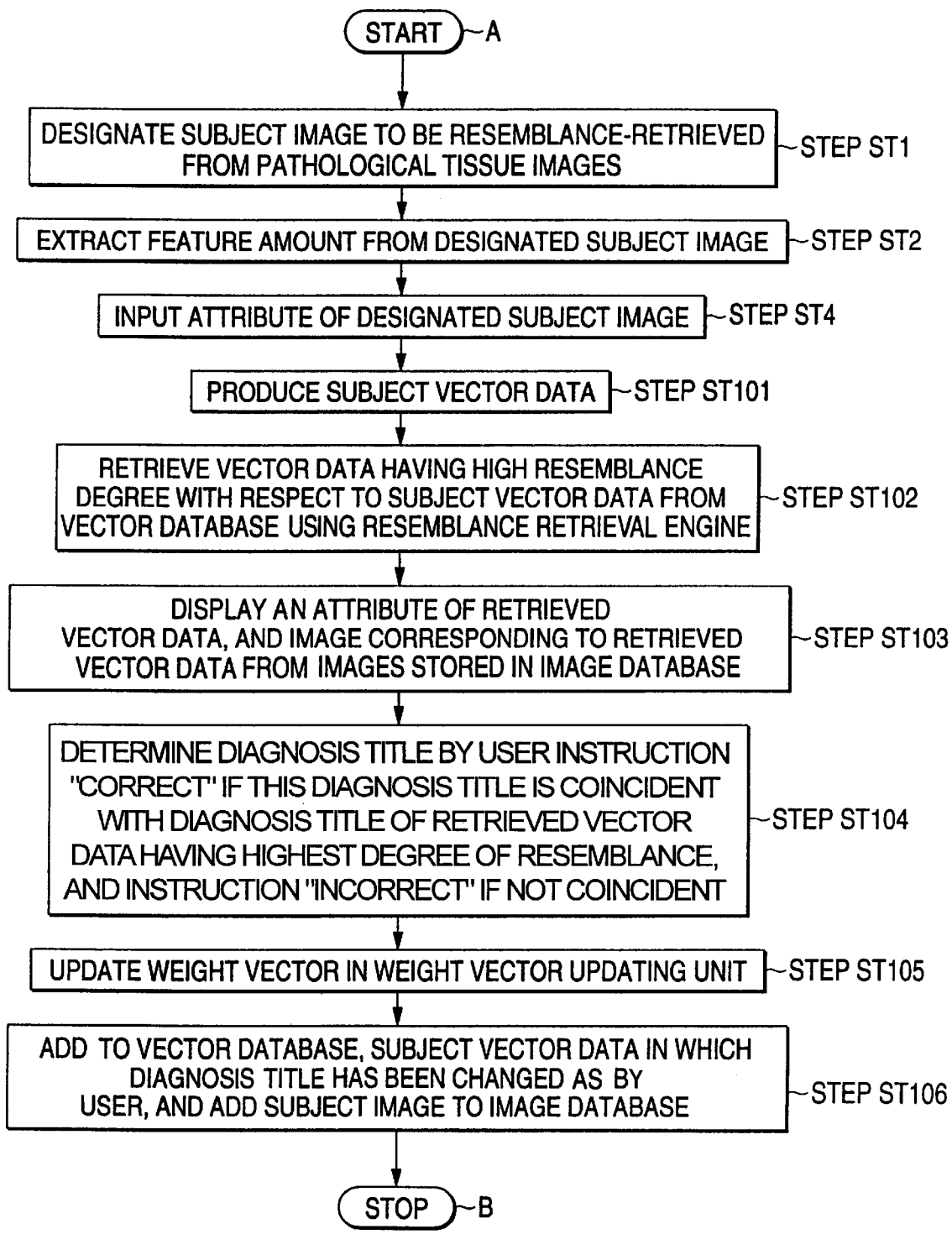
FIG. 9 is a flow chart for describing operations of the conventional resemblance retrieval apparatus.

FIG. 7 is a schematic block diagram showing a resemblance retrieval apparatus according to a second embodiment of the present invention, namely, an example of a resemblance retrieval not employing an image. For this second embodiment, a description is now given of retrieval of diagnostic data from diagnostic patient data.

In this diagram, a plurality of attributes, for instance, patient name, patient ID, patient age, occupation, fever, existence/absence of a cough, existence/absence of nasal mucous, existence/absence of a sore throat, and a diagnosis title, are input into an attribute input unit 4. Vector data, in which these attributes are vector elements, are formed in a subject vector data forming unit 5. Since the diagnosis title has not been determined at this stage, no diagnosis title is entered. For example, such diagnoses titles as a cold and pollen disease are input into a retrieval condition set forming unit 6 as a retrieval condition. Each of the retrieval conditions entered into the retrieval condition set forming unit 6 are used as vector data for a retrieval. Vector data having a high degree of resemblance with respect to the subject vector data are retrieved from the vector database 7 using a weight vector corresponding to the retrieval condition from the weight vectors in the weight vector database 9. As in the first embodiment, in this second embodiment, the optimum weights, which have been previously registered in the vector database 9 with respect to each of the retrieval conditions, are employed.

As previously described in detail, in accordance with a first aspect of the invention, the resemblance retrieval apparatus comprises a vector database storing a plurality of vector data for a plurality of subjects and a plurality of attributes characterizing the subjects as vector elements; a subject vector data forming unit forms vector data with respect to a designated resemblance retrieval subject; a retrieval condition set forming unit forms a plurality of retrieval conditions; a resemblance retrieval engine retrieves vector data which satisfy the retrieval conditions and resemble the subject data from the plurality of vector data stored in the vector database, with respect to each of the retrieval conditions; and a retrieval result display unit displays the vector data retrieved by the resemblance retrieval engine. As a result, resemblance data corresponding to the respective retrieval conditions that the user wants are retrieved and displayed. There is a low possibility that important resemblance data are dropped from the retrieval result.

In accordance with a second aspect of the invention, the resemblance retrieval apparatus comprises an image database storing a plurality of subject images corresponding to a plurality of subjects; a vector database stores a plurality of vector data for each of the subjects, both a feature quantity quantitatively indicating a feature of the subject image and an attribute characterizing the subject are vector elements; a subject vector data forming unit forms vector data based upon an image and an attribute of a designated resemblance retrieval subject; a retrieval condition set forming unit forms a plurality of retrieval conditions; a resemblance retrieval engine retrieves vector data which satisfy the retrieval conditions and resemble the subject data from the vector data stored in the vector database for each of the retrieval conditions; and a retrieval result display unit displaying the vector data retrieved by the resemblance retrieval engine. There is a low probability that important resemblance data, in combination with an image, are dropped from the retrieval results. Also, the resemblance image can be displayed together with the vector data.

In accordance with a third aspect of the invention, the resemblance retrieval apparatus further comprises at least one of a feature quantity extracting unit for extracting a feature quantity of an image, and a feature quantity input unit for inputting a feature quantity of an image, wherein, as a feature quantity for quantitatively indicating a feature of an image, at least one of a feature quantity extracted by the feature quantity extracting unit and a feature quantity input through the feature quantity input unit is employed. As a consequence, a feature quantity subjectively determined by the user can be used in addition to the feature quantities extracted from the image. A feature quantity which is difficult to extract may be utilized, and the resemblance retrieval accomplished based upon the user's choice.

In accordance with a fourth aspect of the invention, in the resemblance retrieval apparatus, an image of biological tissue may be used and, as the retrieval condition, a diagnosis title employed. Accordingly, pathological tissue diagnosis is effectively supported. In particular, as to a rarely used diagnosis title, at least one set of images is displayed, selected from an image for this rarely used diagnosis title for an image resembling a subject image. Therefore, there is a low risk that this rarely used diagnosis title is mistakenly disregarded. As to diagnosis titles for ambiguous images, all of the resemblance images pertinent to these ambiguous images can be displayed. As a result, the risk of making a mistaken diagnosis can be reduced by comparing these ambiguous images with each other.

In accordance with a fifth aspect of the invention, in the resemblance retrieval apparatus, at least one of two feature quantities may be employed; the first feature quantity is calculated employing a quantity representing nuclear a region, area of the nuclear region, shape of the nuclear region, circular degree of the nuclear region, color of the nuclear region, chromaticity of the nuclear region, quantity of an air space region, area of the air space region, shape of the air space region, circular degree of the air space region, quantity of an interstitial region, area of the interstitial region, shape of the interstitial region, circular degree of the interstitial region, color of the interstitial region, chromaticity of the interstitial region, quantity of a tubular region, area of the tubular region, shape of the tubular region, circular degree of the tubular region, texture of an image, and a wavelet transformation value. The wavelet transformation feature quantity is calculated employing the degree to which an epithelium cell represents a two-layer structure in combination with a muscular epithelium cell; degree of texture; existence/absence of nipple pattern; existence/absence of mesh-shaped pattern; existence/absence of a necrotic substance; existence/absence of a fulfill pattern; color of an image; and chromaticity of the image. As a consequence, retrieval precision in pathological diagnosis can be further increased.

In accordance with a sixth aspect of the invention, the resemblance retrieval apparatus further comprises a weight vector database storing a plurality of weight vectors corresponding to each of the retrieval conditions. The weight vectors employed by the resemblance retrieval engine are specified with respect to the respective retrieval conditions. As a consequence, the retrieval precision in the pathological diagnosis can be further increased.

Furthermore, in accordance with the first aspect of the invention, a recording medium has recorded therein a resemblance retrieval program for subject vector data forming, forming vector data in which a plurality of attributes characterizing resemblance retrieval subjects are vector elements; retrieving vector data resembling subject vector data and satisfying the retrieval condition from a plurality of vector data with respect to the subjects stored in a vector database; and outputting the retrieved results for each of the retrieval conditions. There is a low possibility that important resemblance data will be dropped from the retrieval results.

In accordance with the second aspect of the invention, the recording medium has recorded therein a resemblance retrieval program for subject vector data forming, forming vector data based on an image of a resemblance retrieval subject and an attribute characterizing the subject, in which a feature quantity quantitatively indicating a feature of a subject image and the attribute of the subject are vector elements; retrieving vector data resembling subject vector data and also satisfying the retrieval condition from a plurality of vector data with respect to subjects stored in a vector database as retrieval conditions; and outputting the retrieved results for each of the retrieval conditions in combination with the corresponding images. There is a low possibility that important resemblance data, in combination with images, will be dropped from the retrieval results. The resemblance image can be displayed together with the resembled vector data.

What is claimed is:

1. A resemblance retrieval apparatus comprising:
   an image database storing subject images corresponding to respective subjects;
   a vector database storing vector data for each of the subjects, the vector data including vector elements corresponding to respective attributes characterizing each of the subjects and a feature quantity quantitatively indicating a feature of a corresponding subject image;

a subject vector data forming unit for forming vector data, the vector data being based upon an image and attribute, for a subject of a resemblance retrieval with respect to the vector data stored in the vector database;

a retrieval condition set forming unit for forming a plurality of retrieval conditions;

a vector weight database storing weight vectors corresponding to respective retrieval conditions;

a resemblance retrieval engine communicating with the vector database, the subject vector data forming unit, the retrieval condition set forming unit, and the vector weight database, and retrieving the vector data from the vector database most closely satisfying the retrieval conditions as weighted by the weight vectors and thereby most closely resembling the subject of the resemblance retrieval; and a retrieval result display unit communicating with the resemblance retrieval engine and the image database for simultaneously displaying the subject images corresponding to the vector data for each of the subjects that is retrieved by the resemblance retrieval engine from the vector database using the corresponding weight vectors and a corresponding image retrieved from the image database.

2. The resemblance retrieval apparatus of claim 1, further comprising at least one of a feature quantity extracting unit for extracting a feature quantity of an image stored in the image data base, and a feature quantity input unit for inputting a feature quantity of an image stored in the image data base, communicating with the subject vector data forming unit to supply as a feature quantity for quantitatively indicating a feature characterizing an image, at least one of the feature quantity extracted by the feature quantity extracting unit and the feature quantity input from the feature quantity input unit.

3. The resemblance retrieval apparatus of claim 1, wherein the images stored in the image database are images of biological tissue and a diagnosis title in a pathological tissue diagnosis is employed as a retrieval condition.

4. The resemblance retrieval apparatus of claim 3, wherein the feature quantity of the images of biological tissue is selected from the group consisting of quantity of a nuclear region;
area of the nuclear region;
shape of the nuclear region;
circular degree of the nuclear region;
color of the nuclear region;
chromaticity of the nuclear region;
quantity of an air space region;
area of the air space region;
shape of the air space region;
circular degree of the air space region;
quantity of an interstitial region;
area of the interstitial region;
shape of the interstitial region;
circular degree of the interstitial region;
color of the interstitial region;
chromaticity of the interstitial region;
quantity of a tubular region
area of the tubular region;
shape of the tubular region;
circular degree of the tubular region;
texture of an image;
feature quantity obtained from a wavelet transformation value;
degree by which an epithelium cell represents a two-layer structure in combination with a muscular epithelium cell;
degree of texture;
existence of nipple pattern;
existence of mesh-shaped pattern;
existence of a necrotic substance;
existence of a fulfill pattern;
color of an image; and
chromaticity of the image.

5. A recording medium having recorded therein a resemblance retrieval program for causing a computer to execute a process including storing subject images corresponding to respective subjects in an image database;

storing vector data for each of the subjects in a vector database, the vector data including vector elements corresponding to respective attributes characterizing the subjects and a feature quantity quantitatively indicating a feature of a corresponding subject image;

forming vector data, the vector data being based upon an image and attribute, for a subject of a resemblance retrieval with respect to the vector data stored in the vector database;

forming a plurality of retrieval conditions;

storing weight vectors corresponding to respective retrieval conditions in a vector weight database;

retrieving the vector data from the vector database most closely satisfying the retrieval conditions as weighted by the weight vectors and thereby most closely resembling the subject of the resemblance retrieval; and simultaneously displaying the subject images corresponding to the vector data for each of the subjects that is retrieved from the vector database using the corresponding weight vectors and a corresponding image retrieved from the image database.

* * * * *